United States Patent
Watanabe

(10) Patent No.: US 6,811,769 B2
(45) Date of Patent: Nov. 2, 2004

(54) ORAL COMPOSITION, METHOD OF MAKING THE ORAL COMPOSITION AND ORAL HYGIENE METHOD IN JAPANESE AND CHINESE HERBAL REMEDY

(76) Inventor: Shuji Watanabe, 1118, Shimoyamaguchi, Hayama-cho, Mura-gun, Kanagawa-ken (JP)

( * ) Notice: Subject to any disclaimer, the term of this patent is extended or adjusted under 35 U.S.C. 154(b) by 50 days.

(21) Appl. No.: 10/305,028

(22) Filed: Nov. 27, 2002

(65) Prior Publication Data

US 2004/0037790 A1 Feb. 26, 2004

(30) Foreign Application Priority Data

Aug. 23, 2002 (JP) ........................................ 2002-244286

(51) Int. Cl.⁷ ................................................ A61K 7/26
(52) U.S. Cl. ...................................................... 424/58
(58) Field of Search ..................................... 424/49, 58

(56) References Cited

U.S. PATENT DOCUMENTS 5,637,290 A * 6/1997 Sodis et al. .................... 424/49
6,506,406 B1 * 1/2003 Shioya ........................ 424/451

FOREIGN PATENT DOCUMENTS

| JP | 06-157259 | 6/1994 |
| JP | 2002-029982 | 1/2002 |
| WO | WO 00/18380 * | 4/2000 |

OTHER PUBLICATIONS

Martindale, The Extra Pharmacopoeia, 28ᵗʰ ed. published 1982 by The Pharmaceutical Press (London), pp 494 and 691.*

Chrysoula C. Tassou et al., Antimicrobial Activity of the Essential Oil of Mastic Gum (*Pistacia lentiscus* var. *chia*) on Gram Positive and Gram Negative Bacteria in Broth and in Model Food System, *International Biodeterioration and Biodegradation*, 1995, 411–420.

"Periodontal disease can be prevented and treated by oneself", attributed to Shuji Watanabe, published by Makino Shuppan, 1999, pp. 86–91.

Shuji Watanabe, *Tradition & Medicine, vol. 8, No. 1, 2002, pp. 14–15.*

* cited by examiner

*Primary Examiner*—Raymond J. Henley, III
(74) *Attorney, Agent, or Firm*—McGinn & Gibb, PLLC

(57) ABSTRACT

An oral composition includes an oil extract of mastic and an antiphlogistic. An oral hygiene method includes brushing teeth with a dentifrice to which the oral composition has been added, and gargling with a mouth wash which includes at least one extract of crude drug selected from the group consisting of glycyrrhizae radix (glycyrrhiza), arecae semen (betel nut), myristicae semen (nutmeg) and leonuri herba (leonurus sibiricus).

26 Claims, No Drawings

ORAL COMPOSITION, METHOD OF MAKING THE ORAL COMPOSITION AND ORAL HYGIENE METHOD IN JAPANESE AND CHINESE HERBAL REMEDY

BACKGROUND OF THE INVENTION

1. Field of the Invention

The present invention relates to an oral composition and an oral hygiene method, and more particularly to an oral composition and oral hygiene method that may be used in the prevention and/or treatment of periodontal disease.

2. Description of the Related Art

Periodontal disease is an affliction that may be referred to separately as periodontitis (or also called alveolar pyorrhea) and gingivitis. The incidence of periodontal disease increases with age. Finding a method of preventing and/or treating periodontal disease is one of the most important problems to be solved in the fields of medical and dental science. Of course, finding medicines or methods of preventing dental caries (e.g., tooth decay) is also one of the most important problems to be solved in the fields of medical and dental science.

Bacteria which may cause periodontal disease (hereinafter referred to as periodontal disease-related bacteria) include:

Porphyromonas gingivarlis,
Porphyromonas endodontalis,
Prevotella intermedia,
Fusobacterium nucleaum, and
Actinobacillus actinomycetem comitans.

Bacteria which may cause tooth decay (e.g., dental caries) (hereinafter referred to as tooth decay-related bacteria) include:

Streptococcus mutans,
Streptpcoccus sanguis,
Streptococcus mitis,
Actinomyces viscosus,
Actinomyces naeslundii, and
Lactobacillus casei.

Hitherto to the present invention, gargling with a bactericide is commonly employed for treatment of periodontal disease. However, gargling with such a bactericide causes bactericidal action to affect all the bacteria resided in the oral cavity, thereby causing a transient decrease in the number of bacteria. As a result, the indigenous bacteria beneficial to a human being, which administer the oral immune function, are also controlled together with the periodontal disease-related bacteria.

When the immune function in the entire human body is operating properly, the number of beneficial indigenous bacteria reduced by the bactericide may be raised to the original level in a relatively short period of time. However, when the immune function of a human body is deteriorated by aging or disease, growth of the periodontal disease-related bacteria may exceed that of the indigenous bacteria, thereby resulting in further aggravation of the periodontal disease.

For the prevention and/or treatment of periodontal disease, in addition to cleaning the oral cavity by brushing the teeth, it has been also widely known that enhancement of oral immune function is very important.

For such a reason, it has been desired to develop a medicine useful for the prevention and/or treatment of periodontal disease, which has a selective antibacterial activity capable of sufficiently controlling growth of the periodontal disease-related bacteria but not controlling (e.g., adversely affecting) the beneficial indigenous bacteria.

Under the circumstances, the present inventor found that an oral composition which includes at least two extracts of crude drugs selected from arecae semen (betel nut), *glycyrrhizae radix* (glycyrrhiza), *myristicae semen* (nutmeg) and *leonuri herba* (*leonurus sibiricus*) had the selective antibacterial activity as described above. This is disclosed, for example, in Japanese Laid-open Patent Publication No. H06-157259, hereinafter referred to as the first prior patent application in Japan. Such an oral composition exhibits high antibacterial activity against the periodontal disease-related bacteria, does not deteriorate the oral immune function, and has an action accelerating the healing of the periodontal tissue injured due to periodontal disease and further an action accelerating the growth of fibroblasts (e.g., see Shuji Watanabe, "Periodontal disease can be prevented and treated by oneself", published by Makino Shuppan, 1999).

Further, the present inventor researched the effect of the above-described extracts of crude drugs on the DNA synthesis in human gingival epithelium cells and on the generation of interleukin-8 (IL-8) in human gingival fibroblast cells, and found that the above-described extracts of crude drugs had the DNA synthesis-accelerating effect and IL-8 generation-accelerating effect (Shuji Watanabe, "TRADITION & MEDICINE", Vol. 8, No. 1,2002).

However, this conventional oral composition does not have sufficient antibacterial activity against *actinobacillus actinomycetem* comitans, which is often found in patients suffering from vicious periodontal disease, among the periodontal disease-related bacteria.

Therefore, the present inventor searched for a medicine which had sufficient antibacterial activity against actinobacillus actinomycetem comitans, as well as no adverse effect to the periodontal tissue. As a result, the present inventor found that an oil extract of mastic exhibited high antibacterial activities against not only actinobacillus actinomycetem comitans but also the other periodontal disease-related bacteria and the tooth decay-related bacteria as described above. This is disclosed, for example, in Japanese Laid-open Patent Publication No. 2002-29982, hereinafter referred to as the second patent application in Japan. The present inventor demonstrated for the first time, the antibacterial action of mastic against the periodontal disease-related bacteria and the tooth decay-related bacteria.

"Mastic", which is also called olibanum, is a resinoid exudate obtained from *Pistacia lentiscus* belonging to anacardiaceae, a shrub grown on the coast of the Mediterranean Sea. The mastic resin has a long history from the days of ancient Greece and is used for various purposes. For example, it is used as a gum base for chewing gum, a fragrant material, a food additive, a lustering agent, a coating material, a beverage additive, a coating material for intestines, a medicine, etc. It has been understood that the mastic resin may act to activate the immune system when used for treatment of ulcer, reduction of blood sugar level and cholesterol level, amelioration of diabetes, and treatment of cancer.

The mastic resin has also had applications in the dental field. For example, it has been used as a filler for transiently filling up a carious cavity. Also, it has been believed that the mastic resin acts to strengthen teeth. Further, in the place of origin of the mastic resin, teeth cleaning has been carried out with a toothpick made of Pistacia lentiscus (from which the mastic resin was obtained) since long ago.

Sodis et al. (U.S. Pat. No. 5,637,290) discloses an oral hygiene product (tooth paste or mouth wash) which includes the combination of a toothpaste and an ingredient selected from natural mastic from Chios, extracted mastic oil, and synthetic mastic oil agents. In the invention disclosed by Sodis et al., it is understood that mastic chemically reacts with the polymorph-nucleus causing the gathering of white blood corpuscles, resulting in the increase of the defense system of the tissues in the area, and decreases the formation of plaque and gum disease (periodontal disease). However, Sodis et al. does not disclose nor teach any antibacterial activities of mastic.

SUMMARY OF THE INVENTION

In view of the foregoing problems of the conventional formulations, a purpose of the present invention is to provide a formulation capable of making an oil extract of mastic which may be contained in a high (e.g., higher) concentration and used in the stable state. Another object of the present invention is to develop a method of using the oil extract of mastic and crude drugs, by which superior prevention and/or treatment of periodontal disease can be obtained.

The present inventor studied zealously and as a result, found that it is possible to obtain an oral composition (e.g., an oral composition for prevention and/or treatment of periodontal disease) which includes the oil extract of mastic as a component. Further, the oil extract of mastic can be used in an appropriate amount depending upon the condition of periodontal disease. In addition, the oil extract of mastic can be held in the stable state over a long period of time, such as when the oral composition is made into a formulation capable of being later added to a dentifrice (e.g., a commercially available dentifrice).

Since the oil extract of mastic is an oily matter (oil solution), it is difficult to uniformly mix it with a toothpaste or mouth wash. Therefore, conventional toothpastes or mouth washes on the market, such as the product disclosed by the Sodis patent discussed above, have an upper limit on the content of the oil extract of mastic. Specifically, the mastic-containing toothpastes on the market only contain less than 1% by weight of the oil extract of mastic. Further, when a conventional toothpaste mixed with the oil extract of mastic is stored for a long period of time, the oil component is sometimes separated from the toothpaste. Furthermore, the concentration of the oil extract of mastic in conventional toothpastes (e.g., in an amount of less than 1% by weight) is too low to sufficiently prevent and/or treat periodontal disease.

In addition, the present inventor found that by gargling with a mouth wash containing an extract of crude drug after brushing with a dentifrice to which the oral composition of the present invention has been added, the extract of crude drug is absorbed through the oral mucosa and the oral immune function is activated, to effectively prevent and/or treat of periodontal disease which is superior to conventional compositions. The present invention is attained on the basis of these findings.

Namely, in a first aspect of the present invention, an oral composition for prevention and/or treatment of periodontal disease includes an oil extract of mastic (olibanum) and an antiphlogistic as active ingredients.

In the first aspect of the present invention, the oral composition may be preferably used by adding it to a dentifrice (e.g., a commercially available dentifrice). The oil extract of mastic may preferably include an extract prepared by extracting mastic with an olive oil or palm oil. The antiphlogistic may preferably be at least one kind of agent selected from the group consisting of glycyrrhizic acid and salts thereof, glycyrrhezic acid and salts thereof, and tranexamic acid.

The antiphlogistic may more preferably be at least one kind of agent selected from the group consisting of glycyrrhizic acid and salts thereof. The salt of glycyrrhizic acid is preferably at least one kind of agent selected from the group consisting of dipotassium glycyrrhizinate, monoammonium glycyrrhizinate, diammonium glycyrrhizinate, disodium glycyrrhizinate and trisodium glycyrrhizinate. Specifically, the antiphlogistic may more preferably be dipotassium glycyrrhizinate. In particular, dipotassium glycyrrhizinate may preferably be derived from an extract of *glycyrrhizae radix* (glycyrrhiza).

The oral composition for prevention and/or treatment of periodontal disease of the present invention may further include at least one extract of crude drug agent selected from the group consisting of *glycyrrhizae radix* (glycyrrhiza), *lithospermi radix* (gromwell), *myristicae semen* (nutmeg), *arecae semen* (betel nut), *artemisia princeps* (mugwort), *phellodendri cortex* (phellodendron bark), *moutan cortex* (moutan bark), *sctellariae radix* (scutellaria root), *rhei rhizoma* (rhubarb), *chrysanthemum indicum* (wild chrysanthemum) and *leonuri herba* (*leonurus sibiricus*).

The oral composition for prevention and/or treatment of periodontal disease of the present invention may preferably include the oil extract of mastic in an amount of 1% by weight or more. Specifically, the oral composition for prevention and/or treatment of periodontal disease of the present invention may preferably include the oil extract of mastic in an amount of from 3 to 10% by weight.

In a second aspect of the present invention, a method of prevention and/or treatment of periodontal disease includes brushing a person's (e.g., a patient's) teeth with a dentifrice (e.g., commercially available dentifrice) to which the inventive oral composition for prevention and/or treatment of periodontal disease (e.g., according to the first aspect of the present invention) has been added, and then gargling with a mouth wash which includes at least one extract of crude drug selected from the group consisting of *glycyrrhizae radix* (glycyrrhiza), *arecae semen* (betel nut), *myristicae semen* (nutmeg) and *leonuri herba* (*leonurus sibiricus*).

The mouth wash preferably may further include at least one extract of crude drug selected from the group consisting of *lithospermi radix* (gromwell), *artemisia princeps* (mugwort), *phellodendri cortex* (phellodendron bark), *moutan cortex* (moutan bark), *sctellariae radix* (scutellaria root), *rhei rhizoma* (rhubarb) and *chrysanthemum indicum* (wild chrysanthemum).

According to a third aspect of the present invention, a kit for prevention and/or treatment of periodontal disease may include the oral composition for prevention and/or treatment of periodontal disease (e.g., according to the first aspect of the present invention); and a mouth wash which includes at least one extract of crude drug selected from the group consisting of *glycyrrhizae radix* (glycyrrhiza), *arecae semen* (betel nut), *myristicae semen* (nutmeg) and *leonuri herba* (*leonurus sibiricus*).

With its novel features, the oral composition of the present invention may include an oil extract of mastic in a higher concentration than in conventional compositions and is more effective at preventing and/or treating periodontal disease than conventional compositions. In addition, the inventive oral hygiene method provides a more effective method for the prevention and/or treatment of periodontal disease than conventional methods.

This application claims priority from Japanese Patent Application No. 2002-244286, filed on Aug. 23, 2002, which is incorporated herein by reference.

DETAILED DESCRIPTION OF THE PREFERRED EMBODIMENTS OF THE INVENTION

In general, the oral composition for prevention and/or treatment of periodontal disease according to the present invention (hereinafter referred to simply as the oral composition of the present invention) may contain an oil extract of mastic (olibanum) and an antiphlogistic as important ingredients. At the time of brushing, the oral composition may be used with an addition to a dentifrice (e.g., a commercially available dentifrice).

The oral hygiene product (in the form of toothpaste or tooth gel) obtained by blending mastic to a toothpaste as disclosed, for example, by Sodis (U.S. Pat. No. 5,637,290) is on the market in the United States and Japan. However, the product is distinct from the oral composition of the present invention in its formulation. For instance, in the present invention, the mastic component may be mixed with a toothpaste before the toothpaste is used to brush teeth.

In contrast, although the oral composition of the present invention may be used alone, it may also be used for brushing teeth after it is added to a dentifrice (e.g., a commercially available dentifrice). Thus, there is no need to mix the oral composition of the present invention with a commercially available dentifrice before it is used to brush teeth. Namely, the oral composition and the dentifrice may be mixed in the oral cavity while a user brushes his teeth.

For example, the oral composition of the present invention may be used by squeezing a tooth paste (e.g., dentifrice) in an appropriate amount onto a toothbrush, and the oral composition of the present invention may be superimposed on the tooth paste in an appropriate amount. The user may then brush his teeth in a usual manner.

In order not only to prevent and/or treat periodontal disease but also to prevent dental caries (e.g., tooth decay), brushing with a dentifrice is important for keeping the oral cavity clean and removing dental plaque from the oral cavity. Furthermore, brushing with a dentifrice is important to facilitating the flow of blood in the gingiva. Although its composition is not necessarily so limited, the oral composition of the present invention does not necessarily contain a polishing agent, a foaming agent and so on, which are of help to cleaning the oral cavity. These components are commonly contained in commercially available dentifrices, for the reason as described below. Therefore, the oral composition of the present invention may preferably be used after adding it to a dentifrice (e.g., a commercially available dentifrice).

Mastic (e.g., an active ingredient) may generally be extracted from the mastic resin with an oil or an organic solvent such as ethanol, which can dissolve the mastic resin, since the mastic resin of the raw material is insoluble in water. The oral composition of the present invention may be used in the oral cavity. Thus, when extracted with an oil or fat, an edible oil or fat safe for a human body is preferably used. Such edible oils include, for example, olive oil, palm oil, soybean oil, cotton seed oil, corn oil, sesame oil, rape seed oil, peanut oil and camellia oil. In addition to the edible oils, safe fats include, for example, triglycerides of medium chain fatty acids.

As the oil extract of mastic which is one of the important components of the oral composition of the present invention, an olive oil extract or a palm oil extract is preferred. Since olive oil and palm oil have excellent permeability into the oral mucosa, they have high absorption efficiency into a human body. Therefore, olive oil and palm oil can improve the effect of mastic. Alternatively, olive oil and palm oil contain volatile fatty acids and water soluble fatty acids in large quantities, thus giving them excellent miscibility with a dentifrice.

A palm oil extract of mastic may be prepared as follows: for example, 100 parts by weight of palm oil is added to 100 parts by weight of mastic resin, and the mixture is stirred with heat on an oil bath at a temperature of approximately 110° C. for about 30 minutes to completely dissolve the mastic resin in the palm oil. Then, the resultant solution is passed through a mesh or the like having openings of about 50 μm to remove impurities, followed by cooling at a temperature of approximately 25° C., to obtain a palm oil extract of mastic which is an oil solution prepared by dissolving mastic into an oil. The maximum ratio (ratio by weight) of mastic resin against an oil is 50:50 at the time of extraction of mastic, and the oil extract of mastic having the maximum ratio is the one having the highest concentration of mastic.

To extract mastic with a substance other than oils, mastic resin is dissolved in, for example, ethanol, and impurities are removed by filtration or the like, followed by drying to volatilize ethanol, to obtain fine mastic powder containing little impurity (e.g., no impurity). The resultant mastic powder may be dissolved in an oil and used as the oil extract of mastic.

As shown in Test Example 1 described below, the palm oil extract of mastic exhibits high antibacterial activities against a variety of periodontal disease-related bacteria and tooth decay-related bacteria. In particular, it also exhibits high antibacterial activity against *actinobacillus actinomycetem comitans* which is frequently found in patients suffering from advanced periodontal disease.

The oil extract of mastic in the oral composition of the present invention may preferably be used in a concentration range within which mastic can fully exhibit its antibacterial activities in the oral cavity and which the oral composition of the present invention is easy to use. The content of the oil extract of mastic (as the 50:50 ratio-oil extract as described above) in the oral composition of the present invention is not less than 0.0001% by weight, preferably not less than 1% by weight, and more preferably from 3 to 10% by weight. Namely, when the oral composition of the present invention contains the oil extract of mastic, for example, in a content of less than 1% by weight, in order to obtain the fully antibacterial activities of mastic, a large amount of the oral composition of the present invention has to be used. On the contrary, when the content of the oil extract of mastic is beyond 10% by weight, a very small amount of the oral composition of the present invention is needed, it being inconvenient to use in both cases.

The ratio (weight ratio) of the oral composition of the present invention to a dentifrice may preferably be selected within a range which is easy to use in the light of the concentration of the oil extract of mastic in the oral composition. Typically, the weight ratio of a dentifrice to the oral component of the present invention is in a range of from 1:0.5 to 1:2.0, preferably a range of from 1:1 to 1:1.5.

The oral composition of the present invention contains an antiphlogistic as another active ingredient. The oil extract of mastic used in the present invention has no antiphlogistic action. Therefore, the use of the oral composition of the present invention in combination with the antiphlogistic is very effective, particularly for treating gingivitis.

The antiphlogistic used in the oral composition of the present invention is not limited, so long as it has an antiphlogistic action and can be used to the oral cavity. For example, the antiphlogistic may include glycyrrhizic acid and salts thereof, glycyrrhezic acid and salts thereof, tranexamic acid, etc. Of these, glycyrrhizic acid and salts thereof are preferred. The salts of glycyrrhizic acid include, for example, dipotassium glycyrrhizinate, monoammonium glycyrrhizinate, diammonium glycyrrhizinate, disodium glycyrrhizinate and trisodium glycyrrhizinate. Dipotassium glycyrrhizinate is particularly preferred.

In addition, a single kind of antiphlogistic described above may be used alone, or two or more kinds of the antiphlogistic may be used in combination.

When for example, glycyrrhizic acid and a salt thereof are used as the antiphlogistic, the concentration of glycyrrhizic acid and the salt thereof in the oral composition of the present invention is usually in a range of 0.01 to 0.25% by weight after converting them into glycyrrhizic acid, and preferably in a range of 0.05 to 0.22% by weight in the light of alleviation of the bitter taste of mastic.

In the oral composition of the present invention, dipotassium glycyrrhizinate is preferably derived from the extract of *glycyrrhizae radix* (glycyrrhiza). The concentration of the extract of *glycyrrhizae radix* in the oral composition of the present invention is usually in a range of from 0.03 to 1.0% by weight, and preferably in a range of from 0.1 to 0.8% by weight. By the use of the extract of *glycyrrhizae radix* containing dipotassium glycyrrhizinate as the antiphlogistic, the antiphlogistic effect and an effect of activating the immune function in the oral cavity can be obtained coincidentally.

To the oral composition of the present invention, a variety of drug extracts (e.g., crude drug extracts) other than the extract of *glycyrrhizae radix* containing dipotassium glycyrrhizinate as the antiphlogistic may be added as optional components. Such optional components may improve the effectiveness of the oral composition of the present invention in prevention and/or treatment of periodontal disease The crude drugs used as optional components may include, for example, *lithospermi radix* (gromwell), *myristicae semen* (nutmeg), *arecae semen* (betel nut), *artemisia princeps* (mugwort), *phellodendri cortex* (phellodendron bark), *moutan cortex* (moutan bark), *sctellariae radix* (scutellaria root), *rhei rhizoma* (rhubarb), *chrysanthemum indicum* (wild chrysanthemum), *leonuri herba* (*leonurus sibiricus*), *Thea sinensis, Cinnamomum cassia* (cinnamon bark), *Caryophylli Flos, uvae urshi folium*, aloe, *Zingiberis Rhizoma*, ginkgo, pomegranate bark, *Carthami Flos, Menthae Herba, Polygomati Rhizome, Plectranthi Harba, Lonicerae Flos, Sophorae Radix*, Geranium Herb, *Houttuyniae Herba, Eriobotrya japonica, Angelicae Dahuricae Radix, Presicae Semen, Saxifraga stolonifera, Forsythiae Fructus*, white birch, *Humulus lupulus*(hop), lavender, lemon, *Spindus mukurossi, Sasa albo-marginata, Asiasari Radix, Hypericum erectum, Hypericum ascylon*, arnica, *Matricaria chamomilla, Artemisiae Capillari Flos, Arctium lappa, Calendula Officinalis, Calendula arvensis, Centaurea Cyanus, Anthemis nobilis L., Coptidis Rhizoma*, laurel, *Mori Cortex, Salvia officinalis*, thyme, beefsteak plant, *Mentha piperita, Lonicera japonica, Foeniculi Fructus, ECnidii Rhizoma, Aesculus hippocastanum, Aesculus turbinata*, rose and *Zanthoxyli Fructus*.

Of these, *lithospermi radix* (gromwell), *myristicae semen* (nutmeg), *arecae semen* (betel nut), *artemisia princeps* (mugwort), *phellodendri cortex* (phellodendron bark), *moutan cortex* (moutan bark), *sctellariae radix* (scutellaria root), *rhei rhizoma* (rhubarb), *chrysanthemum indicum* (wild chrysanthemum) and *leonuri herba* (*leonurus sibiricus*) are preferred. Particularly, *lithospermi radix* is used as an antipyretic or an antidote in the traditional Chinese medicine, and also for treating of burn injuries or cold injuries. Therefore, it may preferably be added to the oral composition of the present invention because of its action to accelerate the healing of the periodontal tissue injured due to periodontal disease. *Myristicae semen* and *leonuri herba* having DNA synthesis-accelerating effect and IL-8 generation-accelerating effect, which can further improve the effectiveness of the inventive composition in treating periodontal disease, are particularly preferred.

To the oral composition of the present invention, a variety of additives may be added other than the components described above within the effective range for improving the effectiveness of the present invention.

The oral composition of the present invention may have the form of a liquid, paste, gel or the like, and may have a viscosity within an acceptable level so that the liquid, paste or gel does not run when disposed on a toothbrush. In addition to the edible oils used for extraction of mastic, other bases usable to make the oral composition of the present invention, including, for example, silica, calcium carbonate, dental dibasic calcium phosphate and hydroxyapatite. Of these, silica, calcium carbonate and dental dibasic potassium phosphate are preferred.

Binders which impart viscosity to the oral composition of the present invention include, for example, Xanthan gum, cellulose gum, Carrageenan, polyvinyl pyrrolidone and sodium alginate. Of these Xanthan gum and cellulose gum are preferred.

In order for the oil extract of mastic to go throughout the oral cavity at the time of brushing while admixing with moisture in the oral cavity and the dentifrice, an emulsifier is preferably included in the oral composition of the present invention particularly, in a liquid form. Such emulsifiers include, for example, sodium lauryl sulfate, polyoxyethylene hydrogenated castor oil, polysorbates and sucrose fatty acid ester. Polyoxyethylene hydrogenated caster oil and polysorbates are particularly preferred.

The oral composition of the present invention may include, in addition to the additives described above, other additives which may be orally used such as solvents, fragrant materials, refrigerants, sweetening agents, coloring agents, surface active agents, lubricants, thickening agents, pH regulators, preservatives and medical components. It is preferred to employ a solvent having good biocompatibility such as ethanol or water.

The perfumes include, for example, terpenes such as menthol, peppermint oil, spearmint oil, orange oil, lemon oil, eucalyptus oil, mentha oil, acacia oil, fennel oil, bitter almond oil, calamus oil, camphorate oil, cinnamon oil, cassia bark oil, cinnamon leaf oil, rose oil, sandalwood oil, clove oil, herbal oil, banana oil, apple oil, methyl salicylate, carvone, anethole and limonene; and blending perfume materials.

The sweetening agents may include, for example, saccharin, sodium saccharate, xylitol, stevioside, extract of stevia, revaudioside, p-methoxy cinnamic aldehyde, neohesverisyl hydroxy carcon, perillartine, thaumatin, glycyrrhizin, monoglucoside glycyrrhizinate, hernandulcin, trehalose, aspartame and sorbit.

The coloring agents may include, for example, colors designated (e.g., under Japanese law) such as Blue No. 1 and Yellow No. 4, titanium dioxide, and caramel.

The surface active agents may include, for example, anionic surface active agents, cationic surface active agents, ampholytic surface active agents and nonionic surface active agents. Specifically, such agents may include, for example, an alkyl sulfate, an alkyl benzene sulfonate, a sucrose fatty acid ester, a lactose fatty acid ester, a salt of lauroyl sarcosinc, a salt of N-acyl glutamic acid, α-olefin sulfonate, 2-alkyl-N-carboxy-N-hydroxyethylimidazorium betaine, a salt of N-acyltaurine, alkylol amide, polyoxyethylene sorbitan fatty acid ester, polyoxyethylene hydrogenated castor oil and fatty acid ester thereof, polyglycerin fatty acid ester, sorbitan fatty acid ester, fatty acid ester, polyethylene glycol fatty acid ester, and propylene glycol fatty acid ester.

The lubricants may include, for example, sugar alcohols such as sorbitol, maltitol, xylitol and lactitol; and polyhydric alcohols such as glycerin, 1,3-butyleneglycol, 1,2-pentanediol, polyethylene glycol, polypropylene glycol and dipropylene glycol.

The thickening agents may include, for example, carboxy vinyl polymer, sodium carboxymethyl cellulose, methyl cellulose, hydroxyethyl cellulose, Carrageenan, alkali metal salts of alginic acid such as sodium alginate; gums such as gellan gum, xanthan gum, cyamoposis gum, tragacanth gum, karaya gum, aluminum magnesium silicate and gum arabic; polyvinyl alcohol, polyvinyl pyrrolidone, silica gel and aluminum silica gel.

The pH regulators may include, for example, organic acids such as citric acid, malic acid, phosphoric acid and acetic acid and salts thereof; sodium carbonate, sodium hydrogen carbonate, potassium carbonate, potassium hydrogen carbonate, calcium carbonate, calcium hydrogen carbonate, ammonium carbonate, ammonium hydrogen carbonate, potassium sodium carbonate, lithium carbonate, urea, amino acid oligomers, sodium chloride; calcium salts of inorganic acids such as calcium chloride, calcium nitrate, calcium sulfate, calcium glycerophosphate and sodium hydroxide; calcium salts of organic acids such as calcium lactate, calcium acetate, calcium malonate, calcium citrate, calcium gluconate, calcium glycerinate, calcium tartrate and calcium phytate.

The preservatives may include, for example, p-hydroxybenzoates such as methyl paraben, ethyl paraben, butyl paraben, isopropyl paraben and propyl paraben; benzoates such as sodium benzoate; alkyl-diaminoethyl glycin hydrochloride, phenoxy ethanol and sorbic acid.

The medical components may include, for example, allantoin, tocopherol acetate, iso-propyl-methyl-phenol, dextrase, chlorophyll, sodium copper chlorophyll, flavonoid, mutanase, lysozyme, amylase, protease, lytic enzymes, superoxide dismutaze, epsilon aminocaproic acid, aluminum allantoin, aluminum chloro-hydroxy-allantoin, dihydrocholestanol, bisabolol, glycerophosphate, water soluble inorganic phosphorylated compounds; fluorides such as sodium fluoride, sodium monofluorophosphate, stannous fluoride, potassium fluoride, sodium fluosilicate, aluminum fluoride, silver fluoride, hexyl amine hydrofluorate, decanol amine hydrofluorate and oleyl amine hydrofluorate; edetic acid, zinc citrate, zinc chloride, copper gluconate, chlorhexidine gluconate, copper chloride, polyphosphate, pyrophosphate; vitamins such as vitamin A, vitamin C, vitamin E, vitamin B6 and pantothenate; amino acids such as glycin, lysine and histidine; sodium chloride, sodium bicarbonate, aluminum lactate, potassium nitrate, sarcosinate; polyphenol compounds such as catechins; and crude drugs.

The dentrifice (e.g., the commercially available dentifrice) to which the oral composition of the present invention may be added, is not particularly limited and may be any type of dentifrice. As the type of dentifrice, there exists a toothpaste, a tooth gel, a tooth powder and other forms. The oral composition of the present invention can be applied to any type of dentifrice.

The method of prevention and/or treatment of periodontal disease (hereinafter referred to simply as the method of the present invention) is described below. Specifically, the method of the present invention may include brushing a person's (e.g., a patient's) teeth with a dentifrice (e.g., a commercially available dentrifice) to which the inventive oral composition for preventing and/or treating periodontal disease has been added; and then gargling with a mouth wash which includes at least one extract of crude drug selected from the group consisting of glycyrrhizae radix (glycyrrhiza), arecae semen (betel nut), myristicae semen (nutmeg) and leonuri herba (leonurus sibiricus).

According to the inventive method, in addition to brushing with the dentifrice to which the oral composition of the present invention has been added, the oral cavity may be rinsed by gargling with the mouth wash including an extract of crude drug as a component, to permit control of the growth of periodontal disease-relating bacteria which may reside, for example, in a position where a toothbrush cannot reach.

Further, as described above, the present inventor demonstrated that gargling with the mouth wash including an extract of crude drug can control the growth of periodontal disease-relating bacteria without deterioration of the immune function in the oral cavity (e.g., see Japanese Laid-open Patent Publication No. H06-157259, the first prior patent application in Japan). However, the extract of crude drug can not control actinobacillus actinomycetem comitans.

Under such circumstances, the combination of gargling with the mouth wash including an extract of crude drug, and brushing with a dentifrice (e.g., a commercially available dentrifice) to which the oral composition of the present invention including an oil extract of mastic having high antibacterial activities even against actinobacillus actinomycetem comitans and an antiphlogistic as active ingredients has been added, makes it possible to control all the main periodontal disease-relating bacteria.

Since mastic does not operate to improve the immune function in the oral cavity, mastic and crude drugs which operate to heighten the immune function of the oral cavity, to accelerate DNA synthesis and to accelerate generation of IL-8, may be used in combination to obtain superior effectiveness in the prevention and/or treatment of periodontal disease.

Now, description will be made of the mouth wash including an extract of crude drug. Specifically, the mouth wash used in the method of the present invention may include at least one extract of crude drug selected from the group consisting of glycyrrhizae radix (glycyrrhiza), arecae semen (betel nut), myristicae semen (nutmeg) and leonuri herba (leonurus sibiricus).

Among the above-described four kinds of crude drugs, glycyrrhizae radix (glycyrrhiza) has an antiphlogistic effect, and is preferred. Myristicae semen (nutmeg) and leonuri herba (leonurus sibiricus) have effects of accelerating DNA synthesis and of accelerating IL-8 generation, and are preferred.

In the present invention, the extract of crude drug includes both a so-called extract obtained by extraction with hot water or the like, and a liquid extract obtained by a percolation method.

The antibacterial activities of the extracts of crude drugs against the periodontal disease-related bacteria are shown in Table 1 below. In the present invention, determination of MIC (Minimal Inhibitory Concentration) was carried out in accordance with the standard method of Japanese Society of Chemotherapy.

TABLE 1

Minimal Inhibitory Concentration (MIC) of Extract of Each Crude Drug Against Periodontal Disease-related Bacteria

| Periodontal Disease-related Bacteria | Minimal Inhibitory Concentration (MIC) | | | |
|---|---|---|---|---|
| | glycyrrhizae radix | arecae semen | myristicae semen | leonuri herba |
| Porphyromonas gingivarlis 381 | 0.25 | 0.25 | 0.25 | 0.5 |
| Porphyromonas endodontalis ATCC12104 | 1.0 | 2.0 | 1.0 | 2.0 |
| Prevotella intermedia ATCC25261 | 2.0 | 1.0 | 1.0 | >2.0 |
| Fusobacterium nucleaum ATCC25580 | 1.0 | 0.5 | 1.0 | 2.0 |
| Actinobacillus actinomycetem comitans ATCC29523 | >2.0 | >2.0 | >2.0 | >2.0 |

The concentration of each extract is expressed in % by weight.

The method of preparing the mouth wash used in the method of the present invention is described below. Specifically, the method of preparing an extract of glycyrrhizae radix (glycyrrhiza), arecae semen (betel nut), myristicae semen (nutmeg) or leonuri herba (leonurus sibiricus) is not particularly limited, and methods commonly used to extract active ingredients of a crude drug may be employed. For example, extraction with hot water may be carried out to obtain a so-called extract, or extraction by the percolation method may be carried out to obtain a liquid extract. Also, the form of the extract of crude drug is not particularly limited, and the extract of crude drug may be employed in a form of a liquid, a sticky extract, powder, granulates or the like.

Specifically, crude drugs may be individually decocted, and then, the solid matter is removed by filtration, followed by concentration of the resultant filtrate to obtain a sticky extract. Any one of the resultant sticky extracts or a mixture of two or more thereof at an appropriate ratio may be, for example, dried to obtain fine particles. Alternatively, any two or more kinds of the crude drugs selected from the above-described four kinds of crude drugs may be mixed in an appropriate ratio and decocted. The solid matter may be removed by filtration followed by concentration of the filtrate to obtain a sticky extract. At the time of using the resultant fine particles or sticky extract, it may be diluted with water to obtain an aqueous mouth wash.

To the mouth wash used in the method of the present invention, in addition to the above-described extracts of the four kinds of crude drugs, lithospermi radix (gromwell), artemisia princeps (mugwort), phellodendri cortex (phellodendron bark), moutan cortex (moutan bark), sctellariae radix (scutellaria root), rhei rhizoma (rhubarb) and chrysanthemum indicum (wild chrysanthemum) may be added. Of these, as described above, lithospermi radix (gromwell) is a crude drug for external application for the purpose of alleviation of fever, detoxication, or healing of burn injuries or cold injuries. Therefore, it may be expected that *lithospermi radix* (gromwell) effectively accelerates amelioration of the periodontal tissue which was injured due to periodontal disease, and therefore, can be expected to improve the effectiveness of the present invention in treating periodontal disease.

A method of preparing an extract of *lithospermi radix* (gromwell) will be described below.

Specifically, to *lithospermi radix* (root of gromwell), hot water at a temperature of approximately 70° C. is added and extracted, followed by concentration under reduced pressure. An appropriate amount of ethanol may be added to the resultant concentrate and cooled followed by filtration to obtain an extract of *lithospermi radix*.

To the mouth wash used in the present invention, which may include extracts of crude drugs, in addition to the above-described active ingredients, additives such as fragrant materials, sweetening agents, solubilizing agents, foaming agents, stabilizing agents, chelating agents and pH regulators may be added.

When carrying out the method of the present invention, the above-described oral composition of the present invention which may be added to a dentifrice, and the mouth wash including extracts of the above-described crude drugs are conveniently and preferably used in the form of a kit.

EXAMPLES

Now, the present invention will be described more specifically with reference to preparation examples and test examples. However, it should be noted that the present invention is in no way limited to these examples.

Preparation Example 1

Preparation of the oral composition including a palm oil extract of mastic and an extract of *glycyrrhizae radix* (glycyrrhiza) as the active ingredients:

(1) Preparation of Palm Oil Extract of Mastic 1000 g of mastic resin and 1000 g of a purified palm oil (manufactured by Sansho Pharmaceutical Co., Ltd.) were mixed and stirred on an oil bath at a temperature of 110° C. for 30 minutes to completely dissolve the mastic resin in the palm oil. Then, the resultant oil solution was passed through a mesh having openings of about 50 $\mu$m to remove impurities. The oil solution was left to cool to a temperature of approximately 25° C. to obtain a palm oil extract of mastic as an oil solution in which mastic was dissolved.

(2) Preparation of Extract of *Glycyrrhizae radix*

To a root of glycyrrhiza, hot water at a temperature of approximately 70° C. was added and decocted. The resultant solution was concentrated under reduced pressure. An appropriate amount of ethanol was added to the concentrate, followed by cooling. The resultant mixture was filtered to obtain an extract of *glycyrrhizae radix*.

(3) Preparation of Composition (Mastic Paste) Which is Added to a Dentifrice (e.g., A Commercially Available Dentifrice).

By the use of the palm oil extract of mastic and the extract of *glycyrrhizae radix*, prepared respectively in the above items (1) and (2), a mastic paste was prepared in accordance with a formulation shown in Table 2 below.

TABLE 2

Formulation of Mastic Paste

| Component | Mixing Ratio (% by weight) |
|---|---|
| Palm oil extract of mastic | 5.00 |
| Extract of glycyrrhizae radix | 0.05 |
| Concentrated glycerin | 30.00 |
| Ethanol | 20.00 |
| Xanthan gum | 3.00 |
| Purified water | remaining amount |

Test Example 1

MIC Antibacterial Test of Palm Oil Extract of Mastic Against Periodontal Disease-relating Bacteria (1) Test Procedure (a) To the palm oil extract of mastic (50% by weight of mastic and 50% by weight of purified palm oil) prepared in Preparation Example 1 (1), ethanol was added to obtain an ethanol solution having a final concentration of 20% by weight. The resultant 20% ethanol solution was diluted to obtain diluted solutions having various concentrations, respectively. After sterilization, the diluted solutions were added to a brain heart infusion (BHI) medium kept at a temperature of 55° C., respectively, to prepare plate culture media.

The BHI medium was modified depending upon the type of test bacteria to have a formulation as follows:

Periodontal disease-relating bacteria: Yeast. hemin. VK1-containing Brain heart Infusion (BHIY+H. VK1 medium), and Yeast. hemin. VK1-containing Brain heart Infusion Agar (BHIY+H. VK1 agar medium).

Tooth decay-relating bacteria and standard bacteria: Brain heart Infusion (BHI medium), and Brain heart Infusion Agar (BHI agar medium).

(b) Fourteen kinds of bacteria as shown in Table 3 below were smeared on each plate culture medium, respectively. The periodontal disease-related bacteria were incubated at a temperature of 37° C. for 3 days under anaerobic condition, and the other bacteria were incubated at the same temperature for the same period of time under aerobic condition.

(c) After the incubation, the minimum concentration (% by weight) of mastic added to the plate culture medium, at which no colony formation was visually observed, was expressed as minimal inhibitory concentration (MIC).

(2) The test results are shown in Table 3 below.

TABLE 3

Minimal inhibitory concentration (MIC) of palm
oil extract of mastic against various kinds of bacteria

| Type | Name of Bacterium | MIC |
| --- | --- | --- |
| Periodontal disease-related bacteria | *Porphyromonas gingivarlis* 381 | <0.005% |
| | *Porphyromonas endodontalis* ATCC35406 | 1.6% |
| | *Prevotella intermedia* ATCC25261 | 1.6% |
| | *Fusobacterium nucleaum* ATCC25580 | <0.005% |
| | *Actinobacillus actinomycetem comitans* ATCC29523 | 0.2% |
| Tooth Decay-related bacteria | *Streptococcus mutans* 6751 | 0.4% |
| | *Streptococcus sanguis* E206 | 0.4% |
| | *Streptococcus mitis* ATCC9811 | 0.4% |
| | *Actinomyces viscosus* ATCC15987 | 0.2% |
| | *Actinomyces naeslundii* ATCC12104 | 0.2% |
| | *Lactobacillus casei* ATCC393 | 0.2% |
| Standard bacteria | *Escherichia coli* MC1061 | 1.6% |
| | *Staphylococcus aureus* 209P | 0.8% |
| | *Bacillus subtilis* | 0.2% |

It is apparent from the results shown in Table 3 that the oil extract of mastic has sufficient antibacterial activities against all the tested periodontal disease-related bacteria and the tooth decay-related bacteria. Particularly, the oil extract of mastic also has very high antibacterial activity against *actinobacillus actinomycetem* comitans at a concentration of as low as 0.2% by weight.

Test Example 2

The mastic paste prepared in the above-described Preparation Example 1 (hereinafter referred to as mastic paste (A)), which contained the palm oil extract of mastic and the extract of *glycyrrhizae radix* as the active ingredients according to the formulation as shown in the above-described Table 2, and a mastic paste only containing the palm oil extract of mastic as the active ingredient (i.e. no extract of *glycyrrhizae radix* was included) (hereinafter referred to as mastic paste (B)) were applied to patients as described below. Namely, the patients brushed their teeth before going to bed with a commercially available toothpaste to which any one of the two kinds of mastic pastes defined above was added. The effect of treating periodontal disease was compared between the two kinds of the mastic pastes and studied.

Patient: K (55 years old)—Observation of Condition in the Oral Cavity:

(1) Depth of periodontal pocket before start of treatment: 4 to 6 mm (2) Depth of periodontal pocket after using the mastic paste (B) containing no extract of *glycyrrhizae radix* for 3 months: 2 to 5 mm Swelling of gingiva was ameliorated to some extent but redness of gingiva remained unchanged.

(3) After the above item (2), depth of periodontal pocket after using the mastic paste (A) containing the extract of *glycyrrhizae radix* for 4 months: 2 to 3 mm Swelling of gingiva was ameliorated and the color of gingiva changed into healthy color of nearly pink.

The mastic paste (B) containing no extract of *glycyrrhizae radix* exhibited the effect of reducing the depth of periodontal pocket, but had little effect on ameliorating the condition of gingivitis. In contrast, the mastic paste (A) containing the extract of *glycyrrhizae radix*, contains dipotassium glycyrrhizinate derived from the extract of *glycyrrhizae radix*, which has high antiphlogistic effect, and can further decrease the depth of periodontal pocket and can ameliorate the condition of gingivitis. Therefore, the oral composition of the present invention which includes an oil extract of mastic and an antiphlogistic as active ingredients is more effective in the treatment of periodontal disease.

Preparation Example 2

Preparation of Mouthwash Including Extracts of Crude Drugs (1) Preparation of Extracts of Crude Drugs

*Arecae semen, glycyrrhizae radix, myristicae semen* and *leonuri herba* were extracted with water, respectively, and the resultant extracts were concentrated. Ethanol was added to the respective concentrated liquid to obtain respective extracts of the crude drugs. One ml of the extract was prepared from 1 g of each crude drug.

(2) Preparation of Mouth Wash Including Extracts of Crude Drugs

The extracts of *arecae semen* (betel nut), *glycyrrhizae radix* (glycyrrhiza), *myristicae semen* (nutmeg) and *leonuri herba* (*leonurus sibiricus*) as prepared in the above item (1) (manufactured by Matsuura Kanpou Kabushiki Kaisha) were mixed and kneaded at a blending ratio of 1:1:1:1 by a conventional method, dried and granulated to obtain a mouth wash in the form of particles. At the time of using the resultant mouth wash, an appropriate amount of the mouth wash was diluted with water for gargling.

Use Example 1

A commercially available tooth paste was placed on a toothbrush in an amount of about 1.5 g, about 1 g of the mastic paste (A) prepared in Preparation Example 1 was placed on the tooth paste, and the usual brushing of teeth was carried out.

Use Example 2

After brushing of teeth in Use Example 1, 1 g of the mouth wash prepared in Preparation Example 2 was dissolved in 100 mL of water. Gargling with the resultant solution was carried out.

Test Example 3

The effects of treating periodontal disease were compared in two cases: (1) the mouth wash including extracts of crude drugs prepared in the above-described Preparation Example 2 was used alone, and (2) the mastic paste (A) prepared in the above-described Preparation Example 1 was used in combination with the mouth wash (e.g., the teeth were brushed with a commercially available toothpaste to which the mastic paste (A) was added, and then gargling with the mouth wash was carried out).

Patient: I (69 years old)—Observation of Condition in the Oral Cavity (1) Depth of periodontal pocket before start of treatment: 5 to 10 mm Discharge of pus was observed at the several sites of the disease.

(2) Depth of periodontal pocket after using the mouth wash alone for 10 months: 4 to 7 mm The Gram-negative bacteria (particularly, *Actinobacillus actinomycetem comitans*) were not sufficiently controlled, thereafter, the mastic paste (A) was used in combination with the mouth wash.

(3) Depth of periodontal pocket after using the mouthwash and the mastic paste (A) in combination for 3 months following the above treatment (2): 2 to 4

The Gram-negative bacteria (particularly, *Actinobacillus actinomycetem comitans*) were effectively controlled, and the discharge of pus was not observed.

Patient: IT (73 years old)—Observation of Condition in the Oral Cavity:

(1) Depth of periodontal pocket before start of treatment: 4 to 6 mm

Discharge of pus was observed at the several sites of the disease.

(2) Depth of periodontal pocket after using mouth wash alone for 7 months: 2 to 5 mm Although in mild sites of the disease, the condition of the disease was stabilized or ameliorated, in moderate sites of the disease, the condition of the disease got worse (discharge of pus continued). Therefore, the use of the mastic paste (A) in combination with the mouth wash was started.

(3) Depth of periodontal pocket after using the mouth wash and the mastic paste (A) in combination for 9 months following the above treatment (2): 2 to 3 mm The condition of the disease was stabilized in all the sites of the disease, and no discharge of pus was observed.

Patient: IM (53 years old)—Observation of Condition in the Oral Cavity:

(1) Depth of periodontal pocket before start of treatment: 5 to 11 mm (2) Depth of periodontal pocket after using the mouth wash alone for 12 months: 3 to 8 mm The Gram-negative bacteria were not sufficiently controlled, and thereafter, the mastic paste (A) was used in combination with the mouth wash.

(3) Depth of periodontal pocket after using the mouth wash and the mastic paste (A) in combination for 10 months following the above treatment (2): 2 to 5 mm The condition of the disease was stabilized in all the sites of the disease.

The combined use of brushing of teeth with a commercially available dentifrice to which the oral composition including an oil extract of mastic and an antiphlogistic as active ingredients was added, and gargling with the mouth wash including extracts of crude drugs resulted in a highly effective treatment even against the site of the disease in which no amelioration had been observed with gargling with the mouth wash alone. Therefore, it can be understood that the combined use particularly brought about very highly effective treatment of patients suffering from severe periodontal disease.

The oral composition for prevention and/or treatment of periodontal disease of the present invention, which includes an oil extract of mastic and an antiphlogistic as active ingredients, exhibits highly efficient treatment, since it contains an oil extract of mastic in a high concentration. Further, the oral composition of the present invention can be used in an appropriate amount depending upon the severity of periodontal disease, thereby periodontal disease can be more properly prevented and/or treated. Furthermore, since the oral composition of the present invention may be added to a dentifrice (e.g., a commercially available dentifrice) at the time of brushing the teeth, separation of the water soluble components of the dentifrice and the oil extract of mastic does not become an issue, and the oral composition of the present invention can be stored in the stable state for a long period of time.

According to the method of the present invention in which brushing of teeth with the oral composition of the present invention including an oil extract of mastic and an antiphlogistic as active ingredients, followed by gargling with the mouth wash including extracts of crude drugs, the effect of prevention and/or treatment of periodontal disease can be improved.

According to the method of the present invention, growth of tooth decay-related bacteria and periodontal disease-relating bacteria including *actinobacillus actinomycetem comitans* which is often found in patients suffering from severe periodontal disease can be strongly controlled. Although mastic itself does not have the effect of activating the immune function in the oral cavity, the crude drugs having the effect of activating the immune function in the oral cavity may be used in combination with mastic, thereby making it possible to effectly prevent and/or treat periodontal disease.

With its novel features, the oral composition of the present invention may include an oil extract of mastic in a higher concentration than in conventional compositions and is more effective at preventing and/or treating periodontal disease than conventional compositions. In addition, the inventive oral hygiene method provides a more effective method for the prevention and/or treatment of periodontal disease than conventional methods.

While the invention has been described in terms of preferred embodiments, those skilled in the art will recognize that the invention can be practiced with modification within the spirit and scope of the appended claims. Specifically, the description above should in no way be construed as limiting the present invention.

Further, applicant specifically states that no amendment to any claim herein should be construed as a disclaimer of any interest in or right to an equivalent of any element or feature of the amended claim.

What is claimed is:

1. An oral composition comprising:
   an oil extract of mastic in an amount sufficient to provide an antibacterial property to said oral composition; and
   an antiphlogistic.

2. The oral composition according to claim 1, wherein said oral composition has an antibacterial action against periodontal disease-related bacteria and against tooth decay-related bacteria.

3. An oral hygiene product comprising:
   a dentifrice; and
   the oral composition according to claim 1.

4. The oral composition according to claim 1, wherein said oil extract of mastic comprises one of an olive oil extract and a palm oil extract.

5. The oral composition according to claim 1, wherein said antiphlogistic comprises at least one agent selected from the group consisting of glycyrrhizic acid and salts thereof, glycyrrhezic acid and salts thereof, and tranexamic acid.

6. The oral composition according to claim 1, wherein said antiphlogistic comprises at least one agent selected from the group consisting of glycyrrhizic acid and salts thereof.

7. The oral composition according to claim 6, wherein said salt of glycyrrhizic acid comprises at least one agent selected from the group consisting of dipotassium glycyrrhizinate, monoammonium glycyrrhizinate, diammonium glycyrrhizinate, disodium glycyrrhizinate and trisodium glycyrrhizinate.

8. The oral composition according to claim 7, wherein said antiphlogistic comprises dipotassium glycyrrhizinate.

9. The oral composition according to claim 8, wherein said dipotassium glycyrrhizinate comprises a glycyrrhizae radix extracted dipotassium glycyrrhizinate.

10. The oral composition according to claim 1, further comprising:
  at least one extract of crude drug agent selected from the group consisting of glycyrrhizae radix, lithospermi radix, myristicae semen, arecae semen, artemisia princeps, phellodendri cortex, moutan cortex, sctellariae radix, rhei rhizoma, chrysanthemum indicum and leonuri herba.

11. The oral composition according to claim 1, wherein a weight percent of said oil extract of mastic is about 1% or more.

12. The oral composition according to claim 11, wherein said weight percent of said oil extract of mastic is in a range of about 3 to about 10%.

13. The oral composition according to claim 1, wherein said oral composition further comprises at least one of a binder, an emulsifier, a solvent, a fragrance, a refrigerant, a sweetening agent, a coloring agent, a surface active agent, a lubricant, a thickening agent, a pH regulator, a preservative and a medical component.

14. The oral composition according to claim 2, wherein said oral composition has an antibacterial action against actinobacillus actinomyetem comitans.

15. An oral composition for prevention or treatment of periodontal disease, the active ingredients of said oral composition comprising:
  an oil extract of mastic in an amount sufficient to provide an antibacterial property to said oral composition; and
  an antiphlogistic.

16. The oral composition of claim 1, wherein said oil extract of mastic comprises about 50 wt % mastic resin and about 50 wt % oil.

17. The oral hygiene product of claim 3, wherein a weight ratio of said dentrifice to said oral composition is in a range from 1:0.5 to 1:2.0.

18. The oral hygiene product of claim 3, wherein a weight ratio of said dentrifice to said oral composition is in a range from 1:1 to 1:1.5.

19. A method of preventing or treating periodontal disease, comprising:
  brushing teeth using an oral composition according to claim 1.

20. The method according to claim 19, further comprising:
  adding said oral composition to a dentrifice.

21. The method according to claim 20, wherein said brushing teeth with said oral composition comprises brushing teeth with said dentifrice and said oral composition.

22. The method according to claim 21, further comprising:
  gargling with a mouth wash which comprises at least one extract of crude drug selected from the group consisting of *glycyrrhizae radix, arecae semen, myristicae semen* and *leonuri herba*.

23. An oral hygiene method comprising:
  brushing teeth with a dentifrice to which an oral composition has been added, said oral composition comprising an oil extract of mastic and an antiphlogistic; and
  gargling with a mouth wash which comprises at least one extract of crude drug selected from the group consisting of glycyrrhizae radix, arecac semen, myristicae semen and leonuri herba.

24. The oral hygiene method according to claim 23, wherein said mouth wash further comprises at least one extract of crude drug selected from the group consisting of lithospermi radix, artemisia princeps, phellodendri cortex, moutan cortex, sctellariae radix, rhei rhizoma and chrysanthemum indicum.

25. A method of making an oral composition, comprising:
  heating an oil and mastic resin mixture to form an oil extract of mastic; and
  combining said oil extract of mastic resin with an antiphlogistic to form said oral composition. said oil extract of mastic being present in an amount sufficient to provide an antibacterial property to said oral composition.

26. An oral hygiene kit comprising:
  an oral composition comprising an oil extract of mastic and an antiphlogistic; and
  a mouth wash comprising at least one extract of crude drug selected from the group consisting of glycyrrhizae radix, arecae semen, myristicac semen and leonuri herba.

* * * * *

UNITED STATES PATENT AND TRADEMARK OFFICE
CERTIFICATE OF CORRECTION

PATENT NO.     : 6,811,769 B2
DATED          : November 2, 2004
INVENTOR(S)    : Shuji Watanabe It is certified that error appears in the above-identified patent and that said Letters Patent is hereby corrected as shown below:

<u>Title page,</u>
Item [75], please delete and insert the follows:
-- Item [75], Inventor: Shuji Watanabe, 1118,
                          Shimoyamaguchi, Hayama-cho,
                          Miura-gun, Kanagawa-ken (JP) --

Signed and Sealed this

Fifteenth Day of February, 2005

JON W. DUDAS
*Director of the United States Patent and Trademark Office*

UNITED STATES PATENT AND TRADEMARK OFFICE
CERTIFICATE OF CORRECTION

PATENT NO. : 6,811,769 B2
DATED : November 2, 2004
INVENTOR(S) : Shuji Watanabe

It is certified that error appears in the above-identified patent and that said Letters Patent is hereby corrected as shown below:

<u>Title page,</u>
Item [76], please delete and insert the follows:
-- Item [76], Inventor: Shuji Watanabe, 1118,
　　　　　　　　　　　Shimoyamaguchi, Hayama-cho,
　　　　　　　　　　　Miura-gun, Kanagawa-ken (JP) --

This certificate supersedes Certificate of Correction issued February 15, 2005.

Signed and Sealed this

Thirty-first Day of May, 2005

JON W. DUDAS
*Director of the United States Patent and Trademark Office*